US009326773B2

(12) United States Patent
Casasanta, Jr. et al.

(10) Patent No.: US 9,326,773 B2
(45) Date of Patent: May 3, 2016

(54) SURGICAL DEVICE INCLUDING BUTTRESS MATERIAL (75) Inventors: Thomas Casasanta, Jr., Kensington, CT (US); Andrew Miesse, Durham, CT (US); Sally Carter, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 737 days.

(21) Appl. No.: 13/358,551

(22) Filed: Jan. 26, 2012

(65) Prior Publication Data

US 2013/0193192 A1  Aug. 1, 2013

(51) Int. Cl.
*A61B 17/068* (2006.01)
*A61B 17/115* (2006.01)
*A61B 17/072* (2006.01)

(52) U.S. Cl.
CPC ......... *A61B 17/115* (2013.01); *A61B 17/07292* (2013.01); *A61B 17/1155* (2013.01); *A61B 2017/07214* (2013.01)

(58) Field of Classification Search
CPC ........ A61B 17/00; A61B 17/04; A61B 17/32; A61B 17/068; A61B 17/072; A61B 17/0684; A61B 2017/07271; A61B 2017/07285; A61B 17/07292; A61B 2017/07278
USPC ..................... 227/175.1, 180.1, 19, 901–902; 606/153, 209, 215
See application file for complete search history.

(56) References Cited

U.S. PATENT DOCUMENTS

| 3,054,406 A | 9/1962 | Usher |
| 3,124,136 A | 3/1964 | Usher |
| 4,347,847 A | 9/1982 | Usher |
| 4,354,628 A | 10/1982 | Green |
| 4,452,245 A | 6/1984 | Usher |
| 4,605,730 A | 8/1986 | Shalaby et al. |
| 4,655,221 A | 4/1987 | Devereux |

(Continued)

FOREIGN PATENT DOCUMENTS

| CA | 2 667 434 | 5/2008 |
| CN | 101310680 A | 11/2008 |

(Continued)

OTHER PUBLICATIONS

International Search Report corresponding to European Application No. EP 05 02 2585.3, completed on Jan. 25, 2006 and mailed on Feb. 3, 2006; 4 pages.

(Continued)

*Primary Examiner* — Gloria R Weeks
*Assistant Examiner* — Justin Citrin (57) ABSTRACT The present disclosure provides a surgical stapling device and a method for joining tissue portions. The surgical stapling device includes a handle assembly and a tubular body portion supported on a distal end of the handle assembly having a staple cartridge assembly containing a plurality of surgical staples in an annular array. An anvil assembly is at a distal end of the stapling device and has a shaft for removably connecting the anvil assembly to the tubular body portion. The anvil assembly and tubular body portion are juxtaposed with respect to one another along the shaft and are arranged so as to be approximated with respect to one another. A support member extends from the tubular body portion towards the anvil assembly and a buttress material is supported by the support member and removably attached to the support member.

7 Claims, 8 Drawing Sheets

(56) References Cited

U.S. PATENT DOCUMENTS

| | | |
|---|---|---|
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,205,459 A | 4/1993 | Brinkerhoff et al. |
| 5,263,629 A | 11/1993 | Trumbull et al. |
| 5,314,471 A | 5/1994 | Brauker et al. |
| 5,333,773 A * | 8/1994 | Main et al. ............... 227/179.1 |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,087,065 B2 | 8/2006 | Ulmsten et al. |
| 7,108,701 B2 | 9/2006 | Evens et al. |
| 7,128,748 B2 * | 10/2006 | Mooradian et al. ............ 606/151 |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,547,312 B2 * | 6/2009 | Bauman et al. ............... 606/151 |
| 7,559,937 B2 | 7/2009 | de la Torre et al. |
| 7,571,845 B2 | 8/2009 | Viola |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Bettuchi et al. |
| 7,722,642 B2 | 5/2010 | Williamson, IV |
| 7,744,627 B2 * | 6/2010 | Orban et al. ................... 606/215 |
| 7,776,060 B2 * | 8/2010 | Mooradian et al. ............ 606/151 |
| 7,793,813 B2 * | 9/2010 | Bettuchi ..................... 227/179.1 |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crows et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban |
| 7,967,179 B2 | 6/2011 | Olson |
| 7,988,027 B2 | 8/2011 | Olson |
| 8,011,550 B2 | 9/2011 | Aranyi |
| 8,016,177 B2 | 9/2011 | Bettuchi |
| 8,016,178 B2 | 9/2011 | Olson |
| 8,028,883 B2 | 10/2011 | Stopek |
| 8,062,330 B2 | 11/2011 | Prommersberger |
| 8,083,119 B2 | 12/2011 | Prommersberger |
| 8,123,766 B2 | 2/2012 | Bauman |
| 8,123,767 B2 | 2/2012 | Bauman |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino |
| 8,178,746 B2 | 5/2012 | Hildeberg et al. |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo et al. |
| 8,231,043 B2 | 7/2012 | Tarinelli |
| 8,235,273 B2 | 8/2012 | Olson |

(56) References Cited

U.S. PATENT DOCUMENTS

| | | |
|---|---|---|
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,869 B2 | 4/2013 | Heinrich |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,646,674 B2 | 2/2014 | Schulte et al. |
| 8,668,129 B2 | 3/2014 | Olson |
| 8,684,250 B2 | 4/2014 | Bettuchi |
| 8,721,703 B2 | 5/2014 | Fowler |
| 8,757,466 B2 | 6/2014 | Olson |
| 8,789,737 B2 | 7/2014 | Hodgkinson |
| 8,820,606 B2 | 9/2014 | Hodgkinson |
| 8,870,050 B2 | 10/2014 | Hodgkinson |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek |
| 9,016,544 B2 | 4/2015 | Hodgkinson et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 2002/0028243 A1 | 3/2002 | Masters |
| 2002/0091397 A1 | 7/2002 | Chen |
| 2003/0065345 A1 | 4/2003 | Weadock |
| 2003/0083676 A1 | 5/2003 | Wallace |
| 2003/0120284 A1 | 6/2003 | Palacios |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2006/0004407 A1 | 1/2006 | Hiles et al. |
| 2006/0135992 A1 | 6/2006 | Bettuchi |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |

(56) References Cited

U.S. PATENT DOCUMENTS

| | | |
|---|---|---|
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0187286 A1* | 7/2010 | Chen et al. ............... 227/180.1 |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1* | 2/2011 | Viola et al. ............... 227/179.1 |
| 2011/0042443 A1* | 2/2011 | Milliman et al. ........ 227/180.1 |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0215132 A1 | 9/2011 | Aranyi |
| 2011/0278346 A1* | 11/2011 | Hull .................. A61B 17/00491 227/180.1 |
| 2012/0074199 A1 | 3/2012 | Olson |
| 2012/0080336 A1 | 4/2012 | Shelton |
| 2012/0083723 A1 | 4/2012 | Vitaris et al. |
| 2012/0187179 A1 | 7/2012 | Gleiman |
| 2012/0197272 A1 | 8/2012 | Oray et al. |
| 2012/0241499 A1 | 9/2012 | Baxter |
| 2012/0273547 A1 | 11/2012 | Hodgkinson et al. |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0256380 A1 | 10/2013 | Schmid et al. |
| 2013/0277411 A1 | 10/2013 | Hodgkinson |
| 2013/0306707 A1 | 11/2013 | Viola |
| 2013/0310873 A1 | 11/2013 | Prommersberger |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0034704 A1 | 2/2014 | Ingmanson |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |

FOREIGN PATENT DOCUMENTS

| | | |
|---|---|---|
| CN | 101332110 A | 12/2008 |
| DE | 1 99 24 311 A2 | 11/2000 |
| DE | 199 24 311 A1 | 11/2000 |
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 256 318 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 | 8/2007 |
| EP | 1 929 958 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 039 308 A2 | 3/2009 |
| EP | 2 090 231 | 8/2009 |
| EP | 2 090 244 | 8/2009 |
| EP | 2 090 252 | 8/2009 |
| EP | 2 163 211 A2 | 3/2010 |
| EP | 2 189 121 A1 | 5/2010 |
| EP | 2 198 787 A1 | 6/2010 |
| EP | 2 236 098 A2 | 10/2010 |
| EP | 2 236 099 | 10/2010 |
| EP | 2 258 282 A2 | 12/2010 |
| EP | 2 292 276 A2 | 3/2011 |
| EP | 2 311 386 | 4/2011 |
| EP | 2 436 348 | 4/2012 |
| EP | 2 462 880 | 6/2012 |
| EP | 2 497 431 A1 | 9/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 105 A1 | 7/2013 |
| EP | 2 620 106 | 7/2013 |
| EP | 2 630 922 | 8/2013 |
| EP | 2 644 125 | 10/2013 |
| EP | 2 762 091 A2 | 8/2014 |
| JP | 2000-166933 | 6/2000 |
| JP | 2002-202213 | 7/2002 |
| JP | 07-124166 | 5/2007 |
| WO | WO 90/05489 A1 | 5/1990 |
| WO | WO 95/16221 | 6/1995 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 03/082126 A1 | 10/2003 |

(56) References Cited

FOREIGN PATENT DOCUMENTS

| WO | WO 03/088845 | 10/2003 |
|---|---|---|
| WO | WO 03/094743 | 11/2003 |
| WO | WO 03/105698 | 12/2003 |
| WO | WO 03/105698 A2 | 12/2003 |
| WO | WO 2005/079675 | 9/2005 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

International Search Report corresponding to European Application No. EP 06 00 4598, completed on Jun. 22, 2006; 2 pages.
International Search Report corresponding to European Application No. EP 06 01 6962.0, completed on Jan. 3, 2007 and mailed on Jan. 11, 2007; 10 pages.
International Search Report corresponding to International Application No. PCT/US05/36740, completed on Feb. 20, 2007 and mailed on Mar. 23, 2007; 8 pages.
International Search Report corresponding to International Application No. PCT/US2007/022713, completed on Apr. 21, 2008 and mailed on May 15, 2008; 1 page.
International Search Report corresponding to International Application No. PCT/US2008/002981, completed on Jun. 9, 2008 and mailed on Jun. 26, 2008; 2 pages.
International Search Report corresponding to European Application No. EP 08 25 1779, completed on Jul. 14, 2008 and mailed on Jul. 23, 2008; 5 pages.
International Search Report corresponding to European Application No. EP 08 25 1989.3, completed on Mar. 11, 2010 and mailed on Mar. 24, 2010; 6 pages.
International Search Report corresponding to European Application No. EP 10 25 0639.1, completed on Jun. 17, 2010 and mailed on Jun. 28, 2010; 7 pages.
International Search Report corresponding to European Application No. EP 10 25 0715.9, completed on Jun. 30, 2010 and mailed on Jul. 20, 2010; 3 pages.
International Search Report corresponding to European Application No. EP 05 80 4382.9, completed on Oct. 5, 2010 and mailed on Oct. 12, 2010; 3 pages.
International Search Report corresponding to European Application No. EP 10 25 1437.9, completed on Nov. 22, 2010 and mailed on Dec. 16, 2010; 3 pages.
International Search Report corresponding to European Application No. EP 09 25 2897.5, completed on Feb. 7, 2011 and mailed on Feb. 15, 2011; 3 pages.
International Search Report corresponding to European Application No. EP 10 25 0642.5, completed on Mar. 25, 2011 and mailed on Apr. 4, 2011; 4 pages.
International Search Report corresponding to European Application No. EP 11 18 8309.6, completed on Dec. 15, 2011 and mailed on Jan. 12, 2012; 3 pages.
Extended European Search Report corresponding to EP 13 17 7437.4, completed Sep. 11, 2013 and mailed Sep. 19, 2013; (6 pp).
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP No. 12 19 1035.0, completed Jan. 11, 2013 and mailed Jan. 18, 2013; 7 pages.
Extended European Search Report corresponding to EP No. 12 18 6175.1, completed Jan. 15, 2013 and mailed Jan. 23, 2013; 7 pages.
Extended European Search Report corresponding to EP No. 12 19 1114.3, completed Jan. 23, 2013 and mailed Jan. 31, 2013; 10 pages.
Extended European Search Report corresponding to EP No. 12 19 2224.9, completed Mar. 14, 2013 and mailed Mar. 26, 2013; 8 pages.
Extended European Search Report corresponding to EP No. 12 19 6911.7, completed Apr. 18, 2013 and mailed Apr. 24, 2013; 8 pages.
Extended European Search Report corresponding to EP 12 19 8776.2, completed May 16, 2013, and dated May 27, 2013; 8 pages.
International Search Report corresponding to European Application No. EP 12 15 2229.6, completed on Feb. 23, 2012 and mailed on Mar. 1, 2012; 4 pages.
International Search Report corresponding to European Application No. EP 12 15 0511.9, completed on Apr. 16, 2012 and mailed on Apr. 24, 2012; 7 pages.
International Search Report corresponding to European Application No. EP 12 15 2541.4, completed on Apr. 23, 2012 and mailed on May 3, 2012; 10 pages.
International Search Report corresponding to European Application No. EP 12 16 5609.4, completed on Jul. 5, 2012 and mailed on Jul. 13, 2012; 8 pages.
International Search Report corresponding to European Application No. EP 12 15 8861.0, completed on Jul. 17, 2012 and mailed on Jul. 24, 2012; 9 pages.
International Search Report corresponding to European Application No. EP 12 16 5878.5, completed on Jul. 24, 2012 and mailed on Aug. 6, 2012; 8 pages.
Extended European Search Report corresponding to EP 12 19 1035.0, completed Jan. 11, 2013 and mailed Jan. 18, 2013; 7 pages.
Extended European Search Report corresponding to EP 12 19 6904.2, completed Mar. 28, 2013 and mailed Jul. 26, 2013; 8 pages.
Extended European Search Report corresponding to EP 12 19 8749.9, completed May 21, 2013 and mailed May 31, 2013; 8 pages.
Extended European Search Report corresponding to EP 07 00 5842.5, completed May 13, 2013 and mailed May 29, 2013; 7 pages.
Extended European Search Report corresponding to EP 13 15 6297.7, completed Jun. 4, 2013 and mailed Jun. 13, 2013; 7 pages.
Extended European Search Report corresponding to EP 13 17 3985.6, completed Aug. 19, 2013 and mailed Aug. 28, 2013; 6 pages.
Extended European Search Report corresponding to EP 13 17 3986.4, completed Aug. 20, 2013 and mailed Aug. 29, 2013; 7 pages.
Extended European Search Report corresponding to EP 08 72 6500.5, completed Feb. 20, 2014 and mailed Mar. 3, 2014; (7 pp).
Extended European Search Report corresponding to EP 13 19 5919.9, completed Feb. 10, 2014 and mailed Mar. 3, 2014; (7 pp).
Extended European Search Report corresponding to EP 13 19 2123.1, completed Jan. 30, 2014 and mailed Feb. 10, 2014; (8 pp).
Extended European Search Report corresponding to EP 13 19 6816.6, completed Mar. 28, 2014 and mailed Apr. 9, 2014; (9 pp).
Extended European Search Report corresponding to EP 13 19 4995.0, completed Jun. 5, 2014 and mailed Jun. 16, 2014; (5 pp).
Extended European Search Report corresponding to EP 13 19 5019.8, completed Mar. 14, 2014 and mailed Mar. 24, 2014; (7 pp).
Extended European Search Report corresponding to EP 13 19 2111.6, completed Feb. 13, 2014 and mailed Feb. 27, 2014; (10 pp).
Extended European Search Report corresponding to EP 13 19 7958.5, completed Apr. 4, 2014 and mailed Apr. 15, 2014; (8 pp).
Extended European Search Report corresponding to EP 14 15 6342.9, completed Jul. 22, 2014 and mailed Jul. 29, 2014; (8 pp).

(56) References Cited

OTHER PUBLICATIONS

Extended European Search Report corresponding to EP 14 15 7195.0, completed Jun. 5, 2014 and mailed Jun. 18, 2014; (9 pp).
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and mailed Sep. 17, 2014; (8 pp).
Extended European Search Report corresponding to EP 14 16 8904.2, completed Sep. 10, 2014 and mailed Sep. 18, 2014; (8 pp).
Extended European Search Report corresponding to EP 13 19 4995.0, completed Jun. 5, 2014 and mailed Oct. 13, 2014; (10 pp).
Extended European Search Report corresponding to EP 13 15 4571.7, completed Oct. 10, 2014 and mailed Oct. 20, 2014; (8 pp).
Extended European Search Report corresponding to EP 14 18 1125.7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419.3, completed Mar. 24, 2015 and mailed Mar. 30, 2015; (6 pp).
EP Communication corresponding to EP 12 198 776.2 dated Apr. 7, 2015; 6 pages.
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
European Office Action corresponding to counterpart Int'l Appln. No. EP 12 19 8776.2 dated Jan. 19, 2016.

* cited by examiner

SURGICAL DEVICE INCLUDING BUTTRESS MATERIAL

BACKGROUND

1. Technical Field

The present disclosure relates to buttress materials for use with a surgical stapling device and, more particularly, to a method and structure for attaching a buttress material to a surgical stapling device for use in anastomosis procedures.

2. Background of Related Art

Staples have traditionally been used to replace suturing when joining or anastomosing various body structures such as, for example, the bowel or bronchus. The surgical stapling devices employed to apply these staples are generally designed to simultaneously cut and seal an extended segment of tissue in a patient, thus vastly reducing the time and risks of such procedures.

Linear or annular surgical stapling devices are employed by surgeons to sequentially or simultaneously apply one or more linear rows of surgical fasteners, e.g., staples or two-part fasteners, to body tissue for the purpose of joining segments of body tissue together and/or for the creation of anastomoses. Linear surgical stapling devices generally include a pair of jaws or finger-like structures between which body tissue to be joined is placed. When the surgical stapling device is actuated and/or "fired", firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples. Examples of such surgical stapling devices are described in U.S. Pat. Nos. 4,354,628, 5,014,899 and 5,040,715, the entirety of each of which is incorporated herein by reference.

Annular surgical stapling devices generally include an annular staple cartridge assembly including a plurality of annular rows of staples, typically two, an anvil assembly operatively associated with the annular cartridge assembly, and an annular blade disposed internal of the rows of staples. Examples of such annular surgical stapling devices are described in U.S. Pat. Nos. 5,799,857 and 5,915,616 to Robertson et al., the entirety of each of which is incorporated herein by reference.

In general, an end-to-end anastomosis stapler typically places an array of staples into the approximated sections of a patient's bowels or other tubular organs. The resulting anastomosis contains an inverted section of bowel which contains numerous "B" shaped staples to maintain a secure connection between the approximated sections of bowel.

For most procedures, the use of bare staples, with the staples in direct contact with the patient's tissue, is generally acceptable. The integrity of the tissue will normally serve to prevent the staples from tearing out of the tissue and compromising the sealing before healing has occurred. However, in some surgical operations, surgical supports, e.g., meshes or buttress materials, are employed by surgeons in combination with linear stapling devices to bridge, repair and/or reinforce tissue defects within a patient, especially those occurring in the abdominal wall, chest wall, diaphragm, and other musculo-aponeurotic areas of the body. Examples of suitable surgical supports are disclosed in U.S. Pat. Nos. 3,054,406, 3,124,136, 4,347,847, 4,655,221, 4,838,884, 5,002,551, and 7,942,890, the entirety of each of which is incorporated herein by reference.

When the staples are applied in surgical procedures utilizing surgical supports (i.e., reinforcing material), the legs of the staple typically pass from the cartridge jaw through a layer of the surgical support, and through the patient's tissue before encountering the anvil jaw.

While the surgical supports described above are used in conjunction with linear surgical stapling devices, the need exists for annular support structures for use in conjunction with annular or circular surgical stapling devices, for example, an end-to-end anastomosis stapler such as a Model "EEA™" instrument available from United States Surgical, a Division of Tyco Health-Care Group, LP, Norwalk, Conn. and disclosed in U.S. Pat. No. 5,392,979 to Green et al.

One possible side effect of any end-to-end bowel anastomosis is its tendency to undergo stenosis, which can decrease the diameter of the lumen over time. Accordingly, the need exists for an annular surgical structure which operates in conjunction with any end-to-end, annular, or circular anastomosis or stapling device and assists in keeping open the lumen of the anastomosed bowel or other tubular organ over time.

A need also exists for an annular support structure which operates in conjunction with any end-to-end, annular or circular stapling device to reduce the trauma suffered by the patient, reduce the instances of leakage, reduce the instances of bleeding, and create a relatively strong bond between adjacent body tissues.

SUMMARY

The present disclosure provides a surgical stapling device having support members for supporting and attaching a buttress material thereto and a method of using the same.

In one embodiment, a surgical stapling device for joining tissue portions is disclosed. The surgical stapling device includes a handle assembly and a tubular body portion supported on a distal end of the handle assembly having a staple cartridge assembly containing a plurality of surgical staples in an annular array. An anvil assembly is at a distal end of the surgical stapling device and has a shaft for removably connecting the anvil assembly to the tubular body portion. The anvil assembly and tubular body portion are juxtaposed with respect to one another along the shaft and are arranged so as to be approximated with respect to one another. A support member extends from the tubular body portion towards the anvil assembly and a buttress material is supported by the support member and removably attached to the support member where the buttress material is disposed between the anvil assembly and the staple cartridge assembly.

In one embodiment the buttress material includes an attachment member which extends from the buttress material to the support member and is attachable to the support member to removably secure the buttress material to the support member. In another embodiment, the tubular body portion includes a plurality of support members and the buttress material is removably attachable to the plurality of support members. In another embodiment, the support member is disposed in an opening extending at least partially through the tubular body portion. In another embodiment, the support member extends distally from the opening in an axial direction where a distal end of the support member is substantially radially aligned with a distal face of the tubular body portion. In another embodiment, the buttress material is positioned proximate to a tissue contacting surface of the staple cartridge assembly when the buttress material is attached to the support member.

In one embodiment the tubular body portion includes an elongate member extending axially therefrom and defining a passage extending at least partially therethrough for reception of the shaft of the anvil assembly. In another embodiment, the support member is radially disposed between the elongate member and the staple cartridge assembly. In another embodiment, the tubular body portion further includes a knife disposed between the elongate member and the tubular body portion. The knife is actuatable from a first proximal position to a second distal position to sever the tissue portions during firing of the surgical stapling device. In another embodiment, the support member is radially disposed between the elongate member and the knife.

In another embodiment, a surgical stapling device for joining tissue portions is disclosed. The surgical stapling device includes a handle assembly and a tubular body portion supported on a distal end of the handle assembly having a staple cartridge assembly containing a plurality of surgical staples in an annular array. An anvil assembly is at a distal end of the stapling device and has a shaft for removably connecting the anvil assembly to the tubular body portion. The anvil assembly and tubular body portion are juxtaposed with respect to one another along the shaft and are arranged so as to be approximated with respect to one another. An elongate member extends from the tubular body portion towards the anvil assembly and includes an opening extending at least partially therethrough for receiving the shaft of the anvil assembly. A buttress material is supported by the elongate member and removably attached thereto where the buttress material is disposed between the anvil assembly and the staple cartridge assembly.

In one embodiment, the elongate member defines a substantially circular platform at a distal end thereof and the buttress material is attachable to the circular platform. In another embodiment, the elongate member defines a proximal portion and a distal portion where the distal portion has an outer diameter which is larger than an outer diameter of the proximal portion and the circular platform is disposed on the distal portion. In another embodiment, the inner diameter of the proximal and distal portions are substantially the same. In another embodiment, the buttress material is adhered to a distal end of the elongate member. In another embodiment, a distal end of the elongate member is substantially radially aligned with a distal end of the staple cartridge assembly.

A method of using buttress material with a surgical stapling device is also disclosed. The method including the steps of positioning the buttress material at least partially between an anvil assembly and a cartridge assembly of the surgical stapling device and extending from the cartridge assembly to a support member of the surgical stapling device, securing the buttress material to the support member, receiving body tissue between the anvil assembly and the cartridge assembly, grasping the body tissue between the anvil assembly and the cartridge assembly, and firing the surgical stapling device to drive a plurality of staples from the cartridge assembly through the buttress material and the body tissue to thereby secure a first portion of the buttress material to the body tissue.

In one embodiment, the step of firing the surgical stapling device includes the step of transitioning a knife between a first proximal position and a second distal position to sever the first portion of the buttress material from a second portion of the buttress material which is not secured to the body tissue, the second portion of the buttress material remaining secured to the support member. In another embodiment, the support member is disposed radially inward of the cartridge assembly with the knife disposed therebetween and the step of transitioning the knife includes the step of the knife severing the buttress material extending between the cartridge assembly and the support member. In another embodiment, the second portion of the buttress material is a plurality of attachment members extending from the first portion of the buttress material to the support member and the step of transitioning the knife includes the step of the knife severing the plurality of attachment members from the first portion of the buttress material.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein.

DETAILED DESCRIPTION OF EMBODIMENTS

Embodiments of the presently disclosed annular surgical stapling device will now be described in detail with reference to the drawing figures wherein like reference numerals identify similar or identical elements. As used herein and as is traditional, the term "distal" refers to that portion which is furthest from the user while the term "proximal" refers to that portion which is closest to the user.

Figure 1:
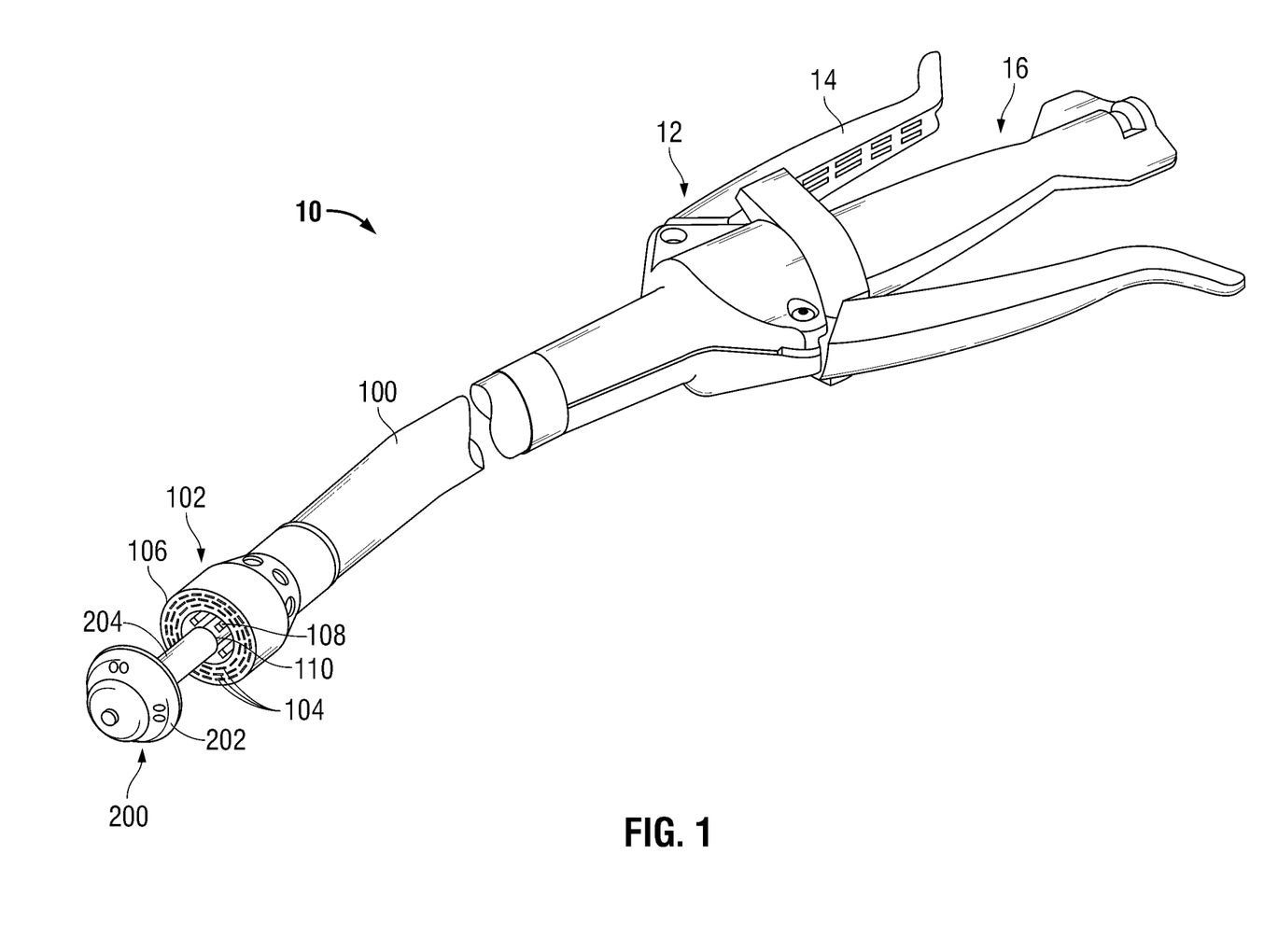
FIG. 1 is a perspective view of an exemplary annular surgical stapling device according to the present disclosure.

Referring initially to FIG. 1, an annular surgical stapling device for use with a buttress material is disclosed herein and is generally designated as 10. Surgical stapling device 10 includes a handle assembly 12 having at least one pivotable actuating handle member 14, and an advancing member 16. Extending from handle member 12, there is provided a tubular body portion 100 which may be constructed so as to have a curved shape along its length. Body portion 100 terminates in a staple cartridge assembly 102 which includes at least one annular array of staple receiving slots 104 having a staple (not shown) disposed in each one of staple receiving slots 104. For example, staple cartridge assembly may include one, two, or more than two annular arrays of staple receiving slots 104.

Staple cartridge assembly 102 may be fixedly connected to the distal end of tubular body portion 100 or may be configured to concentrically fit within the distal end of tubular body portion 100. Typically, staple cartridge assembly 102 includes a staple pusher (not shown) including a proximal portion having a generally frusto-conical shape and a distal portion defining two concentric rings of peripherally spaced fingers (not shown), each one of which is received within one of the respective staple receiving slots 104.

Typically, a knife (not shown), substantially in the form of an open cup with the rim thereof defining a knife edge, is disposed within staple cartridge assembly 102 and mounted to a distal surface of a staple pusher (not shown). The knife edge is disposed radially inward of the pair of annular arrays of staples. Accordingly, in use, as the staple pusher is advanced, the knife is also advanced axially outward.

Positioned distally of staple cartridge assembly 102 there is provided an anvil assembly 200 including an anvil member 202 and a shaft 204 operatively associated therewith for removably connecting anvil assembly 200 to a distal end portion of stapling device 10.

Reference may be made to U.S. Pat. No. 5,915,616 to Viola et al., the entire contents of which are incorporated herein by reference, for a detailed discussion of the construction and operation of annular stapling device 10. U.S. Pat. No. 5,915,616 to Viola et al. is hereby incorporated by reference herein, in its entirety.

Figure 4:
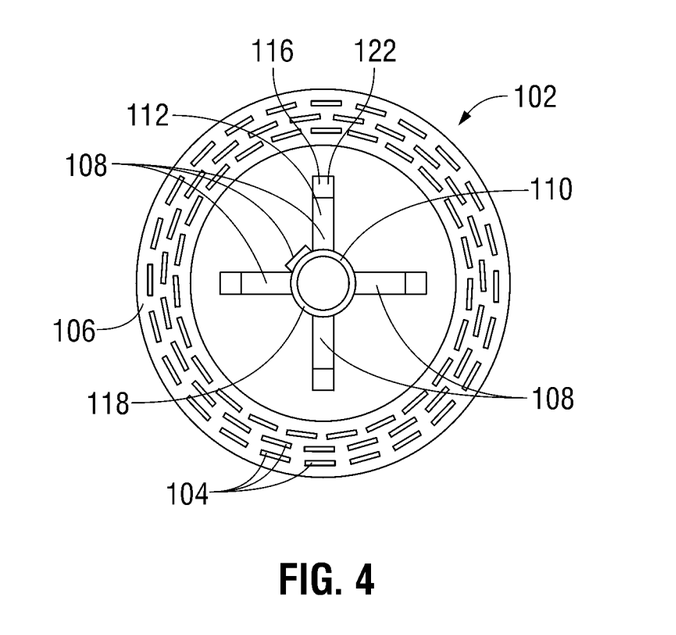
FIG. 4 is a top, plan view of the tubular body portion of FIG. 3, illustrating the support members of an embodiment of the present disclosure.
Figure 5:
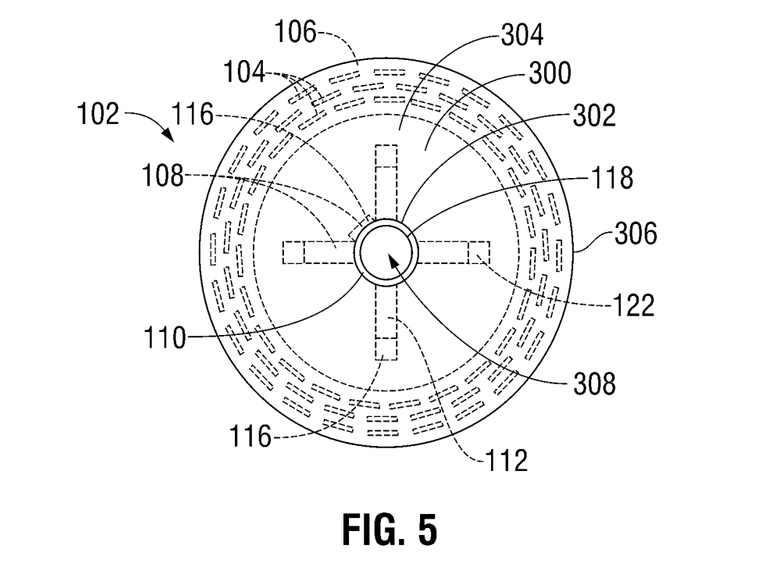
FIG. 5 is a top, plan view of the tubular body portion of FIG. 3, illustrating the buttress material supported on the support members.
Figure 6:
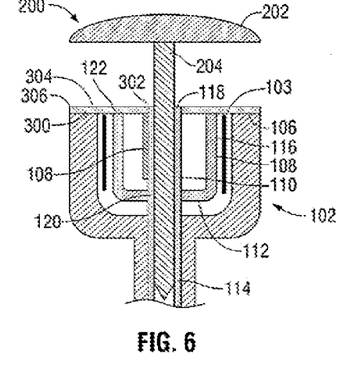
FIG. 6 is a schematic, longitudinal, cross-sectional view of the anvil assembly and tubular body portion of FIG. 3, as taken through 6-6 of FIG. 3, illustrating the buttress material supported on the support members.

Referring now to FIGS. 1, 3, 4, 5 and 6, body portion 100 of stapling device 10 includes a plurality of support members 108 extending from a central shaft 110. One or more support members 108 are adapted to support and secure a buttress material 300 adjacent to or proximate to a tissue contacting surface 106 of staple cartridge assembly 102. As seen in FIG. 6, each support member 108 includes a base portion 112 extending radially outward from a proximal portion 114 of central shaft 110 and an attachment portion 116 extending distally from base portion 112. It is contemplated that each base portion 112 may alternatively extend from central shaft 110 at any position along its length up to and including a distal end 118 of central shaft 110, where, for example, each base portion 112 may extend from central shaft 110 at a middle portion 120 or at distal end 118. It is also contemplated that each support member 108 may extend directly from tubular body portion 100 rather than central shaft 110.

It is contemplated that each attachment portion 116 may be radially spaced from central portion 110 or may be adjacent to or abutting central portion 110 where no base portion 112 would be necessary. Any number of support members 108 may be provided at various positions radially about central portion 110, such as, for example, one, two, four or more support members 108. Support members 108 may be positioned radially about central shaft 110 in any configuration where, for example, each support member may be offset by ninety degrees (See FIGS. 4 and 5) or may be offset by more degrees or less degrees as desired. It is also contemplated that the offset between a first adjacent pair of support members 108 may be greater or less than the offset between a second adjacent pair of support members 108. As seen in FIGS. 4 and 5, attachment portions 116 of each support member 108 may be positioned at a different spacing from central portion 110 and multiple support members 108 having attachment portions 116 with different spacing from central portion 110 may be included at the same time.

Base portions 112 of support members 108 may define a linear shape or may instead define an arcuate shape where, for example, a portion of base portions 112 curve distally away from central portion 110.

Each support member 108 may define a transverse cross-section having a substantially square shape or may define a transverse cross-section having a circular, oval, rectangular, triangular, polygonal or other shape suitable for supporting a buttress material 300 on a distal end 122 of the support member 108. It is contemplated that the transverse cross-section of base portion 112 and attachment portion 116 of each support member 108 may be substantially the same or that the base portion 112 and attachment portion 116 may have different transverse cross-sections.

Distal end 122 of each support member 108 may permanently or removably secure buttress material 300 in place and buttress material 300 may be attached to distal end 122 of each support member 108 by various methods including, for example, adhesives, ultrasonic welding, tacking, stapling, hook and loop, or other methods of attachment which are suitable to either permanently affix or removably affix buttress material 300 to each support member 108.

As seen in FIG. 6, distal end 122 of each support member 108 may be positioned between central shaft 110 and knife 103 and at the same radial plane as tissue contacting surface 106 of staple cartridge assembly 102 relative to central shaft 110 where, when buttress material 300 is affixed or attached to support member 108, buttress material 300 defines a substantially linear radial configuration between support 108 and tissue contacting surface 106 of staple cartridge assembly 102. It is also contemplated that distal end 122 of each support member 108 may be located longitudinally proximal or distal of tissue contacting surface 106 of staple cartridge assembly 102.

Figure 2:
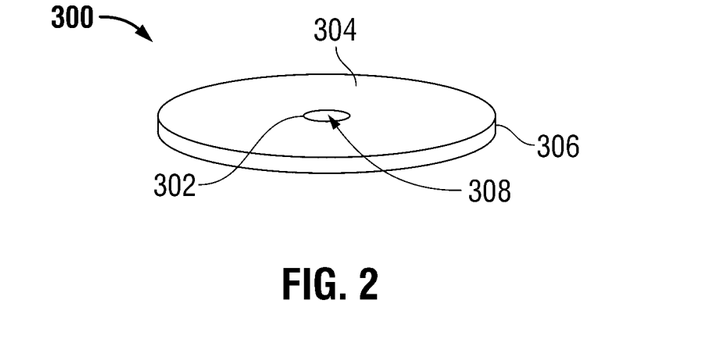
FIG. 2 is a perspective view of a buttress material in accordance with an embodiment of the present disclosure, for use with the annular surgical stapling device of FIG. 1.
Figure 3:
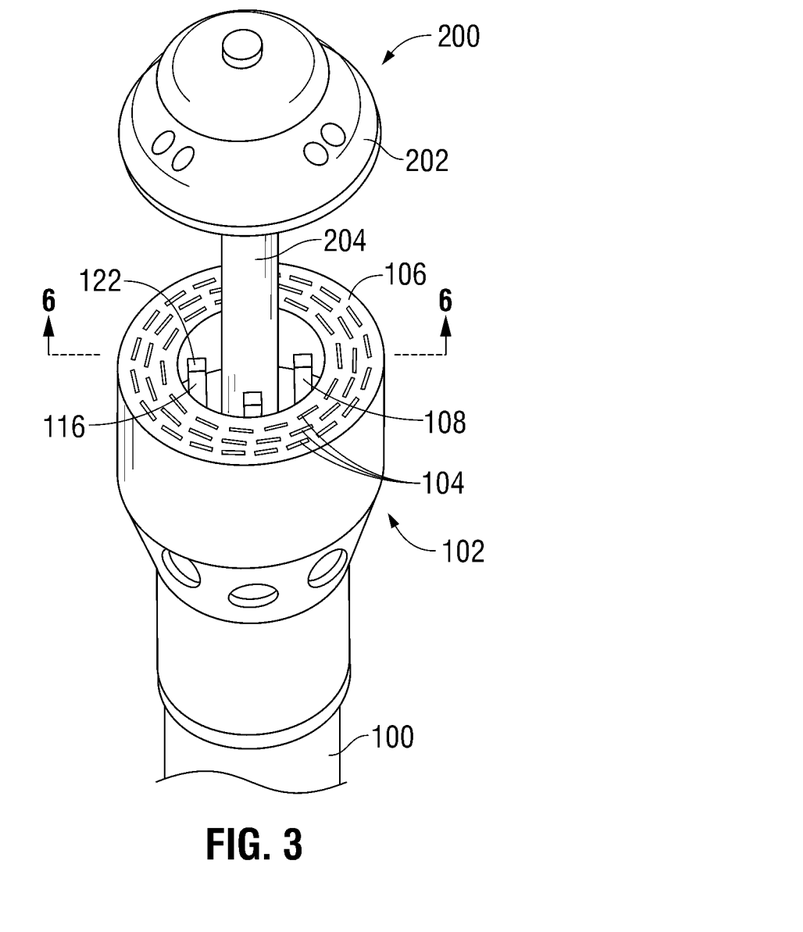
FIG. 3 is an enlarged perspective view of an anvil assembly and a tubular body portion of the annular surgical stapling device of FIG. 1.

Referring now temporarily to FIG. 2, buttress material 300 is generally annular in shape and includes an inner portion 302, a middle portion 304, and an outer portion 306. A substantially centrally located aperture 308, defined by the inner circumference of inner portion 302 is formed through buttress material 300. Buttress material 300 may be any shape sufficient to provide support for anastomosis of tissue after surgical stapling device 10 has been fired including, for example, a square, a circle, an oval, a triangle or any other polygonal or other shape.

In one embodiment, as seen in FIG. 6, buttress material 300 is sized such that when buttress material 300 is affixed or attached to support members 108, outer portion 306 of buttress material 300 extends radially beyond staple receiving slots 104 (See FIGS. 3-5) of staple cartridge assembly 102. Additionally, aperture 308 of buttress material 300 is sized to at least receive shaft 204 of anvil assembly 200 therethrough. Aperture 308 of buttress material 300 may also be sized to receive central shaft 110 of tubular body portion 100 therethrough. In another embodiment, the distance between outer portion 306 of buttress material 300 and inner portion 302 of buttress material 300 is substantially equal to a width of a tissue contacting surface 106 of staple cartridge assembly 102.

Each portion 302, 304, and 306 of buttress material 300 may be fabricated from surgical grade, biocompatible, non-absorbable material (i.e. permanent) or absorbable material (i.e. non-permanent) mesh or material desirably impregnated with an adhesive, sealant and/or other medicament. It is also contemplated that each portion may be a composite of both a non-absorbable and an absorbable material. Suitable materials for the fabrication of buttress material 300 and suitable adhesives, sealants, and/or medicaments for impregnation in or application to buttress material 300 may be found, for example, in U.S. Pat. No. 7,942,890, referenced above. U.S. Pat. No. 7,942,890 is hereby incorporated by reference herein, in its entirety.

Figure 7:
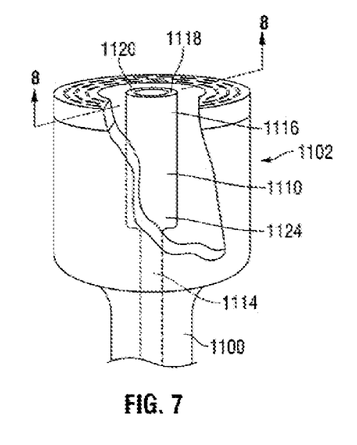
FIG. 7 is a schematic, perspective cut-away view of a tubular body portion of an annular surgical stapling device according to another embodiment of the present disclosure.
Figure 8:
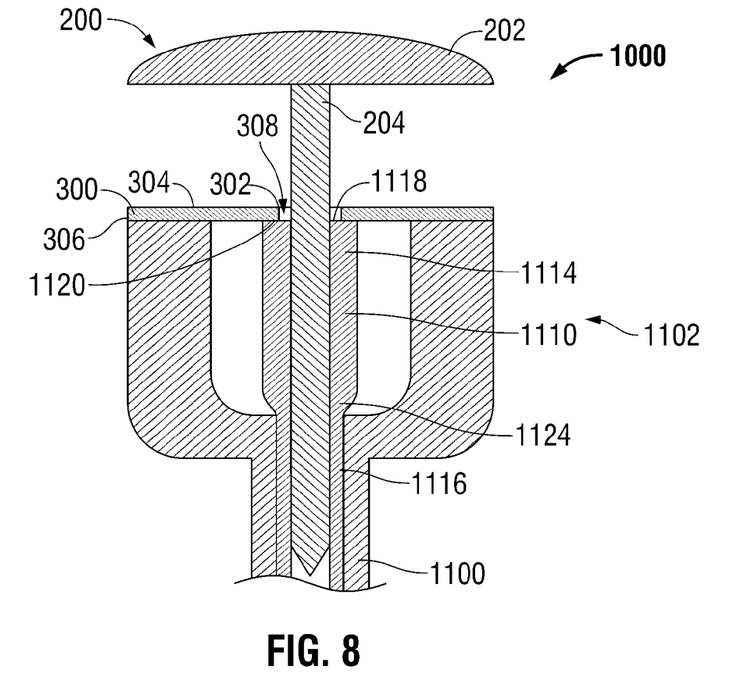
FIG. 8 is a schematic, longitudinal, cross-sectional view of the annular surgical stapling device of FIG. 7, as taken through 8-8 of FIG. 7.
Figure 9:
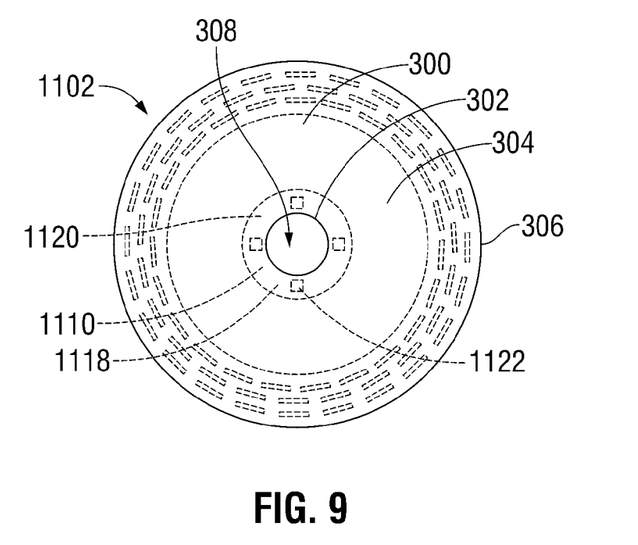
FIG. 9 is a top, plan view of the tubular body portion of FIG. 7, illustrating a buttress material attached to a central shaft of the tubular body portion.

In another embodiment of the present disclosure, as seen in FIGS. 7-9, an annular surgical stapling device 1000 is disclosed including a tubular body portion 1100 which is similar to tubular body portion 100. In this embodiment, a staple cartridge assembly 1102 of tubular body portion 1100 includes a central shaft 1110 having a proximal portion 1114 with a first smaller thickness and a distal portion 1116 with a second larger thickness. For example, central shaft 1110 defines an inner diameter which is substantially the same for both the proximal and distal portions 1114 and 1116 for receiving the shaft 204 of anvil assembly 200. The outer diameter of central shaft 1110 is smaller at the proximal portion 1114 and larger at the distal portion 1116. The difference between the inner and outer diameters defines a platform 1120 at a distal end 1118 of central shaft 1110 for supporting buttress material 300.

Central shaft 1110 may transition from the smaller outer diameter to the larger outer diameter gradually along the longitudinal length of central shaft 1110 where, for example, the outer diameter gradually tapers outward from proximal to distal, or central shaft 1110 may transition from the smaller outer diameter to the larger outer diameter by defining an arcuate transition portion 1124, as seen in FIGS. 7 and 8. It is contemplated that central shaft 1110 may have any configuration for transitioning from the smaller outer diameter at the proximal portion 1114 to the larger outer diameter at the distal portion 1116 to increase the thickness of central shaft 1110 at the distal portion 1116 thereof to provide platform 1120, including, for example, a gentle tapered transition, an arcuate transition, or a radial extrusion from proximal portion 1114.

Platform 1120 may define any shape suitable for providing an attachment surface for securing buttress material 300. For example, platform 1120 may be circular, square, rectangular, triangular, oval, starred, spoked, or any other polygonal shape or suitable shape.

As discussed above, buttress material 300 may be attached to platform 1120 through any means of attachment or affixation including, for example, adhesives, ultrasonic welding, tacking, stapling, hook and loop, or other methods of attachment which are suitable to either permanently affix or removably affix buttress material 300 to platform 1120. For example, platform 1120 may include attachment points 1122 (See FIG. 9) for receiving and securing buttress material 300 to platform 1120. It is contemplated that support members, as described above, may also be included to assist in supporting and affixing buttress material 300. The attachment methods disclosed in U.S. patent application Ser. No. 13/094,893, filed Apr. 27, 2011, may also be used to attach the buttress material to the support member or platform discussed above. U.S. patent application Ser. No. 13/094,893 is hereby incorporated by reference herein, in its entirety. The buttresses disclosed herein may be made from the materials disclosed in U.S. patent application Ser. No. 13/094,893, filed Apr. 27, 2011. U.S. patent application Ser. No. 13/094,893 is hereby incorporated by reference herein, in its entirety.

Figure 10:
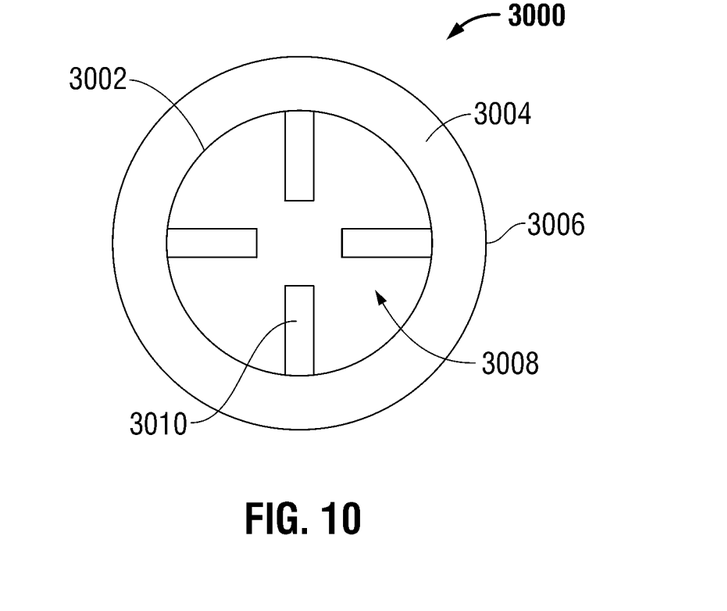
FIG. 10 is a plan view of a buttress material, according to another embodiment of the present disclosure, for use with an annular surgical stapling device.
Figure 11:
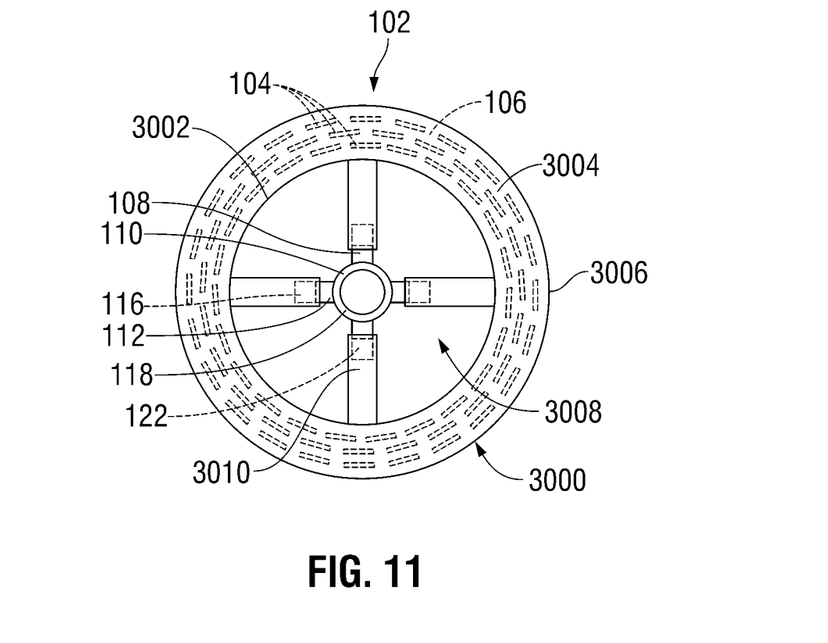
FIG. 11 is a top, plan view of the buttress material of FIG. 10, illustrating the buttress material supported on the support members of a tubular body portion of the annular surgical stapling device.
Figure 12:
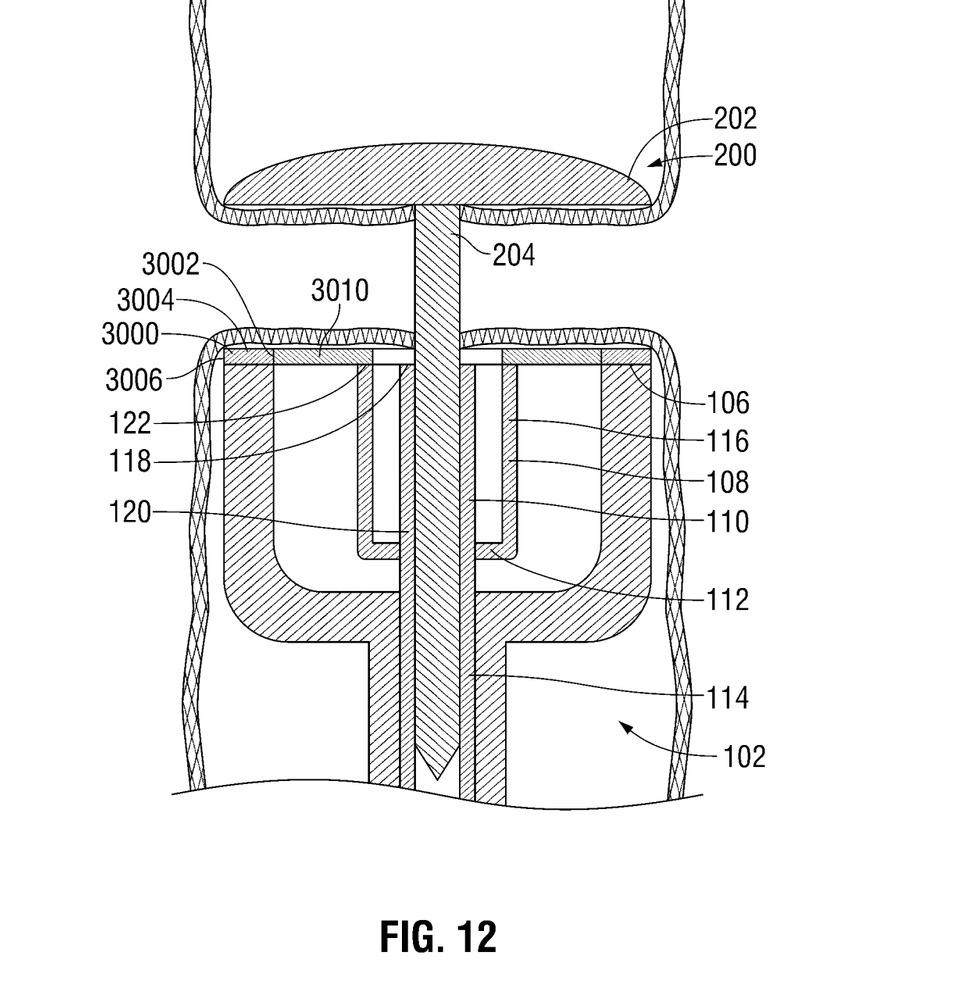
FIG. 12 is a schematic, longitudinal, cross-sectional view of the annular surgical stapling device of FIG. 3, illustrating the buttress material of FIG. 10 supported on the support members of the tubular body portion with tissue disposed between the buttress material and the anvil assembly of the annular surgical stapling device.

In another embodiment of the present disclosure, as seen in FIGS. 10-12, a buttress material 3000 is disclosed which is similar to buttress material 300. Buttress material 3000 includes an inner portion 3002, a middle portion 3004, an outer portion 3006 and defines an aperture 3008 therethrough. In this embodiment, aperture 3008 is substantially larger than central shaft 110 of tubular body portion 100 where, for example, aperture 3008 may have a diameter substantially equal to the inner diameter of staple cartridge assembly 102. It is contemplated that aperture 3008 may also be smaller than the inner diameter of staple cartridge assembly 102.

Buttress material 3000 is configured for positioning adjacent tissue contacting surface 106 of staple cartridge assembly 102 and may define a donut like shape which is substantially equivalent in width to the width of tissue contacting surface 106. It is contemplated that buttress material 3000 may alternatively have a width which is greater than that of tissue contacting surface 106 and that buttress material 300 may extend radially outward past tissue contacting surface 106 and/or radially inward towards support members 108 and central shaft 110.

Buttress material 3000 is securable to support members 108 through the use of a plurality of attachment members 3010 extending from inner portion 3002 into aperture 3008 towards central shaft 110. Attachment members 3010 allow buttress material 3000 to be supported by and attached or affixed to support members 108 with a minimal amount of material. This reduces overall costs for buttress material 3000 and reduces the force necessary to separate attachment members 3010 from the rest of buttress material 3000, during firing by, for example, a knife. Attachment members 3010 may be configured to break away or to be severed from buttress material 3000 after or during firing and may include perforations, shearable sections, or other mechanisms suitable to facilitating the separation of attachment members 3010 from the rest of buttress material 3000.

Attachment members 3010 may be attached or affixed to attachment portion 116 of support members 108 in the same manner as described above with regard to buttress material 300 including, for example, adhesives, ultrasonic welding, tacking, stapling, hook and loop, or other methods of attachment which are suitable to either permanently affix or removably affix attachment members 3010 to support members 108.

Attachment members 3010 may define a rectangular shape or may define other shapes including, for example, triangular, square, semicircular, or other shapes suitable for supporting buttress material 3000 and attaching or affixing buttress material 3000 to support members 108 or platform 1020.

Buttress material 3000 and attachment members 3010 may be made from any of the materials describe above for buttress material 300 and found in U.S. Pat. No. 7,942,890, referenced above. One or more of inner portion 3002, middle portion 3004, outer portion 3006 and attachment members 3010 may be made from the same material or one or more of inner portion 3002, middle portion 3004, outer portion 3006, and attachment members 3010 may be made from different materials.

Figure 13:
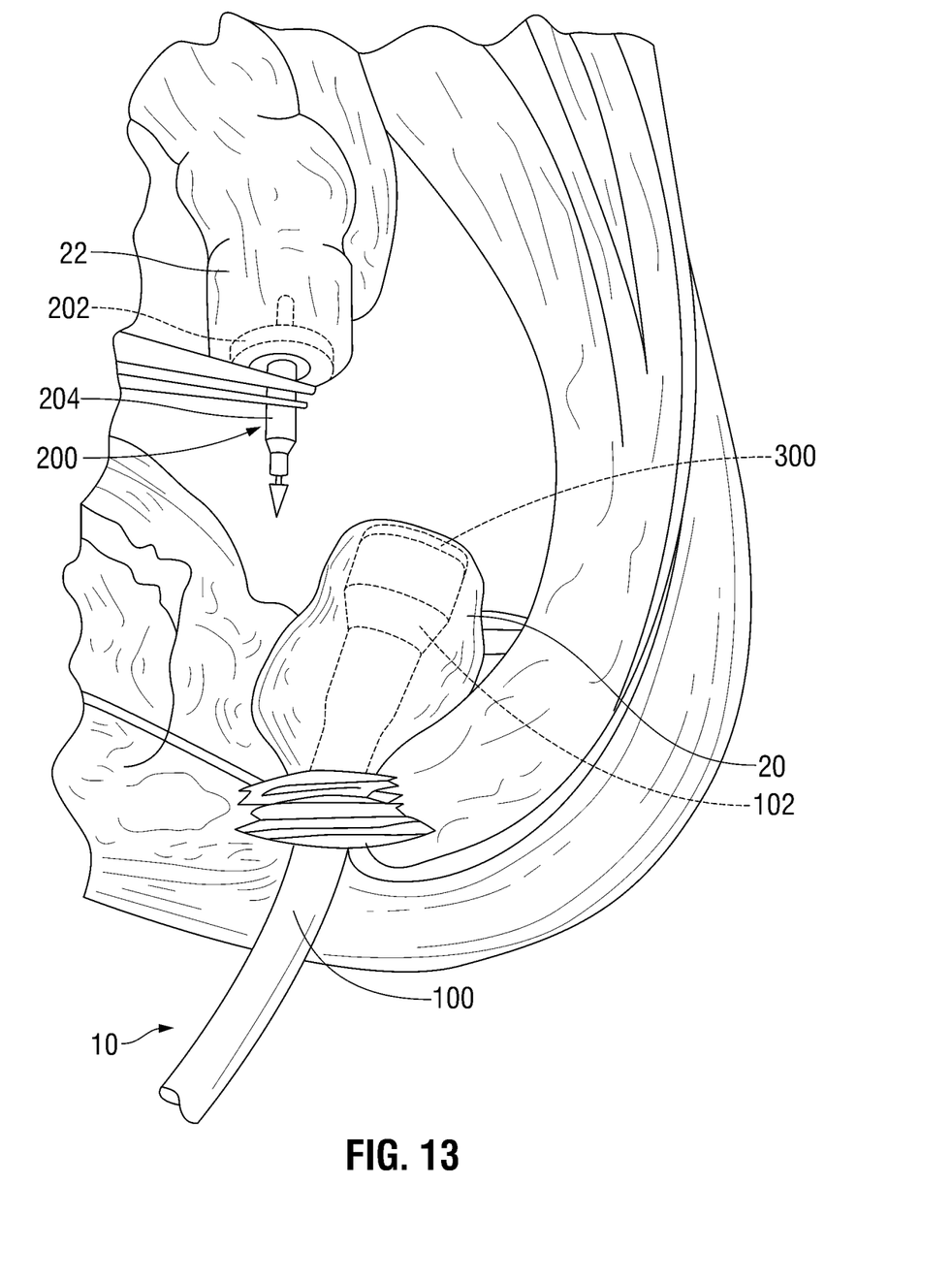
FIG. 13 is a perspective view of the intestinal area of a patient, illustrating a method of positioning the annular surgical stapling device of FIG. 1 to connect the anvil assembly to the tubular body portion.

Turning now to FIGS. 12 and 13, there is illustrated the use of annular surgical stapling device 10 and detachable anvil assembly 200 in an anastomosis procedure to effect joining of intestinal sections 20 and 22. The anastomosis procedure is typically performed using minimally invasive surgical techniques including laparoscopic means and instrumentation. At the point in the procedure shown in FIG. 13, a diseased intestinal section has been previously removed, anvil assembly 200 has been applied to the operative site either through a surgical incision or transanally and positioned within intestinal section 22, and tubular body portion 100 of annular surgical stapling device 10 has been inserted transanally into intestinal section 20. Intestinal sections 20 and 22 are also shown temporarily secured about their respective components (e.g., shaft 204 of anvil assembly 200, and the tissue contacting surface 106 of tubular body portion 100).

According to one method, as seen in FIGS. 6, 8, 12, and 13, buttress material 300 may be placed onto support members 108 of tubular body portion 100 (or platform 1120 of tubular body portion 1000) prior to the coupling of anvil assembly 200 to the central shaft 110 of tubular body portion 100. Tubular body portion 100 may come with buttress material 300 pre-attached to support members 108 (or platform 1120). Alternatively the surgeon may attach buttress material 300 to support members 108 (or platform 1120) prior to use. With buttress material 300 secured in place, the surgeon maneuvers anvil assembly 200 until the proximal end of shaft 204 is inserted into the central shaft 110 of tubular body portion 100. Central shaft 110 is now engaged to shaft 204 with intestinal sections 20 and 22 disposed between anvil assembly 200 and staple cartridge assembly 102. As seen in FIG. 12, for example, buttress material 300 is disposed between cartridge assembly 102 and intestinal sections 20 and 22.

Anvil assembly 200 and tubular body portion 100 are then approximated to approximate intestinal sections 20, 22 and capture buttress material 300 between intestinal section 20 and tissue contacting surface 106 of staple cartridge assembly 102. Surgical stapling device 10 is then fired to staple buttress material 300 and intestinal sections 20, 22 together and the knife is actuated to cut the portion of tissue and buttress material 300 disposed radially inward of the knife, to complete the anastomosis. For example, the knife may cut through a portion of buttress material 300 and may be aligned with perforations or other shearable sections of buttress material 300 to require less force for cutting. Alternatively when a buttress material 3000, having attachment members 3010 is provided, the knife may cut through a portion of each attachment member 3010 near inner portion 3002 of buttress material 3000 where, for example, less force is required to cut through attachment members 3010 than to cut through buttress material 300 because less material is provided in the path of the knife.

While the use of surgical stapling device 10 has been shown and described, it is understood and within the scope of the present disclosure that surgical stapling device 1000 may be operated in the same or similar manner.

While several configurations of support members and platforms have been illustrated and described, it will also be apparent that various modifications can be made without departing from the spirit and scope of the present disclosure. For example, it is envisioned and within the scope of the present disclosure for a greater or smaller number of support members to be provided. It is also envisioned that the spacing of support members from the central shaft may be adjusted and that the spacing or circumferential position of the support members about the central shaft may be adjusted. It is also envisioned that a thicker or thinner central shaft with a larger or smaller platform may be provided.

Thus, it should be understood that various changes in form, detail and application of the buttress materials of the present disclosure may be made without departing from the spirit and scope of the present disclosure.

What is claimed is:

1. A surgical stapling device for joining tissue portions, comprising:
   a handle assembly;
   a tubular body portion supported on a distal end of the handle assembly, the tubular body portion having a staple cartridge assembly containing a plurality of surgical staples in an annular array, and an elongate member extending axially therefrom and defining a distal surface, the staple cartridge assembly defining an inner annular edge, wherein a gap is defined between the inner annular edge of the staple cartridge assembly and the elongate member;
   an anvil assembly at a distal end of the surgical stapling device, the anvil assembly having a shaft for removably connecting the anvil assembly to the tubular body portion, the anvil assembly and tubular body portion being juxtaposed with respect to one another along the shaft and arranged so as to be approximated with respect to one another;
   a support member extending from the tubular body portion towards the anvil assembly, the support member having a proximal end extending radially outward from the elongate member of the tubular body and a distal end extending distally from the proximal end of the support member, wherein the distal end of the support member is radially located in the gap between the inner annular edge of the staple cartridge assembly and the elongate member, and wherein the distal end of the support member is coplanar with and does not extend beyond a tissue contacting surface, wherein the tissue contacting surface is defined by the staple cartridge assembly; and
   a buttress material supported by the support member and removably attached thereto, wherein the buttress material is disposed between the anvil assembly and the staple cartridge assembly, and wherein the buttress material overlays the annular array of surgical staples and extends radially inward of the distal end of the support member such that the distal end of the support member is entirely overlain by the buttress material.

2. A surgical stapling device according to claim 1, wherein the buttress material includes an attachment member extending from the buttress material to the support member, the attachment member being attachable to the support member to removably secure the buttress material to the support member.

3. A surgical stapling device according to claim 1, wherein the tubular body portion includes a plurality of support members, the buttress material being removably attachable to the plurality of support members.

4. A surgical stapling device according to claim 1, wherein the buttress material is positioned proximate to a tissue contacting surface of the staple cartridge assembly when the buttress material is attached to the support member.

5. A surgical stapling device according to claim 1, wherein the elongate member defines a passage extending at least partially therethrough for reception of the shaft of the anvil assembly.

6. A surgical stapling device according to claim 5, wherein the tubular body portion further includes a knife disposed between the elongate member and the tubular body portion, the knife actuatable from a first proximal position to a second distal position to sever the tissue portions during firing of the surgical stapling device.

7. A surgical stapling device according to claim 6, wherein the support member is radially disposed between the elongate member and the knife.

* * * * *